United States Patent
Kwak et al.

(10) Patent No.: US 10,736,987 B2
(45) Date of Patent: Aug. 11, 2020

(54) IMPLANT FOR LYMPH NODE FORMATION/REGENERATION

(71) Applicant: Klinikum rechts der Isar der Technischen Universität München, Munich (DE)

(72) Inventors: Min-Seok Kwak, Munich (DE); Jan-Thorsten Schantz, Langenargen (DE); Dietmar Werner Hutmacher, Belbowrie (AU); Mohit Prashant Chhaya, Munich (DE); Elizabeth Rosado Balmayor, Ried (DE)

(73) Assignee: Klinikum rechts der Isar der Technischen Universität München, Munich (DE)

( * ) Notice: Subject to any disclaimer, the term of this patent is extended or adjusted under 35 U.S.C. 154(b) by 449 days.

(21) Appl. No.: 15/538,654

(22) PCT Filed: Dec. 18, 2015

(86) PCT No.: PCT/EP2015/080516
§ 371 (c)(1),
(2) Date: Jun. 22, 2017

(87) PCT Pub. No.: WO2016/102374
PCT Pub. Date: Jun. 30, 2016

(65) Prior Publication Data
US 2017/0354757 A1    Dec. 14, 2017

(30) Foreign Application Priority Data
Dec. 23, 2014  (EP) .................................... 14200090

(51) Int. Cl.
*A61L 27/18* (2006.01)
*C12N 5/078* (2010.01)
(Continued)

(52) U.S. Cl.
CPC ........... *A61L 27/18* (2013.01); *A61L 27/3604* (2013.01); *C12N 5/0651* (2013.01); *A61L 27/48* (2013.01);
(Continued)

(58) Field of Classification Search
CPC ...... A61L 27/18; A61L 27/3604; A61L 27/48; A61L 27/56; C12N 5/0651;
(Continued)

(56) References Cited

U.S. PATENT DOCUMENTS

2008/0267924 A1  10/2008  Alitalo et al.
2012/0125348 A1   5/2012  Alitalo
2014/0242347 A1   8/2014  Paukshto et al.

FOREIGN PATENT DOCUMENTS

EP   1 454 641 A2   9/2004
JP   2004-243125 A  9/2004
(Continued)

OTHER PUBLICATIONS

International Searching Authority—EPO, International Search Report and Written Opinion, PCT/EP2015/080516; dated Feb. 22, 2016. 11 pages.
(Continued)

*Primary Examiner* — Kara D Johnson
(74) *Attorney, Agent, or Firm* — Sunstein LLP

(57) ABSTRACT

The present invention relates to the field of implants for the formation/regeneration of lymph nodes. In particular, the present invention relates to an implant comprising a biodegradable scaffold and lymph node fragments immobilized therein and/or thereon, to a method of manufacturing such an implant and to uses of such an implant.

24 Claims, 8 Drawing Sheets

(51) Int. Cl.
  *A61L 27/36* (2006.01)
  *A61L 27/48* (2006.01)
  *A61L 27/56* (2006.01)

(52) U.S. Cl.
  CPC ........... *A61L 27/56* (2013.01); *C12N 2513/00* (2013.01); *C12N 2533/30* (2013.01); *C12N 2533/50* (2013.01); *C12N 2533/56* (2013.01); *C12N 2533/80* (2013.01)

(58) Field of Classification Search
  CPC ............ C12N 2513/00; C12N 2533/50; C12N 2533/56; C12N 2533/30; C12N 2533/80
  See application file for complete search history.

(56) References Cited

FOREIGN PATENT DOCUMENTS

| | | |
|---|---|---|
| WO | WO 2013/103423 | 7/2013 |
| WO | WO-2013103423 A2 * | 7/2013 |
| WO | WO 2015/054654 | 4/2015 |
| WO | WO-2015054654 A1 * | 4/2015 |

OTHER PUBLICATIONS

Japanese Patent Office, Notification of Reason for Rejection, Application No. 2017-533897, dated Nov. 1, 2019, with English translation, 9 pages.

* cited by examiner

IMPLANT FOR LYMPH NODE FORMATION/REGENERATION

CROSS-REFERENCE TO RELATED APPLICATIONS

This Application is a U.S. national stage entry under 35 USC § 371 of PCT/EP2015/080516 filed Sep. 18, 2015, which claims priority to European Patent Application 14 200 090.0, filed Dec. 23, 2014; both of which are incorporated herein by reference in their entireties.

FIELD OF THE INVENTION

The present invention relates to the field of implants for the formation/regeneration of lymph nodes. In particular, the present invention relates to an implant comprising a biodegradable scaffold and lymph node fragments immobilized therein and/or thereon, to a method of manufacturing such an implant and to uses of such an implant.

BACKGROUND OF THE INVENTION

The lymphatic system consists of different lymphoid organs (thymus, bone marrow, spleen, lymph nodes, tonsils, appendix, Peyer's patches), a conducting network of lymphatic vessels, and the circulating lymph fluid. Within the body, the lymphatic system fulfills important functions in the removal of interstitial fluid from tissues, the absorption and transport of fatty acids and fats as chyle from the digestive system, or the stimulation of immune responses through antigen-presenting cells (APCs), such as dendritic cells, in the lymph nodes.

The human body comprises altogether between five and six hundred lymph nodes located at intervals along the lymphatic vessels. Many of these lymph nodes are grouped in clusters in different body regions, for example in the underarm and abdominal areas. Lymph nodes are particularly numerous in the mediastinum in the chest, neck, pelvis, axilla (armpit), inguinal (groin) region, and in association with the blood vessels of the intestines. One of their important functions is to filter the interstitial fluid (lymph) of the body region where they are located and to transport the filtered fluid to the blood.

The lymph node is surrounded by a capsule of connective tissue which includes smooth muscle cells, thus allowing the lymph node to contract and to advance the lymph fluid. The core of the lymph node consists of an organized collection of lymphoid tissue formed by a meshwork of reticular cells and fibers with embedded lymph follicles, spherical aggregations of lymphocytes in the meshwork of the reticulum.

Numerous small afferent lymph vessels enter through the capsule of the lymph node, whereas only a single efferent lymph vessel leaves the capsule. The afferent lymph vessels transport lymph to the core of the lymph node, where the lymph is filtered and then drained out by the efferent lymph vessel in order to be returned to the blood. The efferent lymph vessel leaves the capsule at the "hilum", a depression on the surface of the lymph node, which makes the otherwise spherical lymph node, bean-shaped or ovoid. In addition to the efferent lymph vessel, the arteries and veins supplying the lymph node with blood enter and exit at the hilum region.

There are two different types of vessels among the lymph vessels, capillaries and collectors. In contrast to capillaries, collectors are surrounded by smooth muscle cells and include valves, thus ensuring contractile, unidirectional transport of lymph fluid.

If lymph nodes are unable to fulfill their function, this may give rise to lymphedema, a condition characterized by the swelling of body tissue due to the accumulation of lymph fluid in the interstitium. Lymphedema usually affects limbs, though the face, neck and abdomen may also be affected. In extreme cases, lymphedema may even result in an abnormal enlargement of certain body parts (elephantiasis).

Lymphedema often becomes chronic. Frequently, lymphedema is caused by severe infection, in particular by parasitic diseases, such as lymphatic filariasis, or arises as a side effect of cancer therapy (e.g. due to surgical removal of cancerous lymph nodes in the armpit, causing the atm to swell due to poor lymphatic drainage, or groin, causing swelling of the leg, or due to radiotherapy).

At present, no standard curative treatment is available for lymphedema patients, as current practice involves symptomatic care only. Typically, patients are treated by compression garments or massages (lymph drainage). While temporarily reducing the volume of edema by pressing lymph from the edema into body regions with a functioning lymph system, such treatment options only target the symptoms of lymphedema and thus their effects are only transitory.

A generally accepted etiologic surgical standard therapy for the treatment of lymphedema does not exist yet. In recent years, significant success has been reported by an approach in which a lymph node from an unaffected region of the patient's body is transplanted to the body part affected by lymphedema. In this procedure, a lymph node package (lymph node and fat tissue) is removed from the axillary or inguinal region and is transplanted by microsurgical methods to the area affected by lymphedema (Becker et al., 2006). The lymph node's blood supply vessel is connected surgically under the microscope to a recipient vessel in the area of lymphedema, thus ensuring survival of the transplanted lymph node. The surviving lymph node apparently secretes growth factors (VEGF-C) which locally induce formation of new lymph vessels. The transplanted lymph node with newly formed lymph vessels improves the removal of lymph fluid from the affected area, thus causing a significant reduction in the swelling of the affected tissue.

Due to the high demands of the microsurgical procedure, however, this type of operation to transplant a lymph node is an extended surgical intervention of 5-8 hours under general anesthesia which typically involves hospitalization of the patient for at least 5-7 days. Moreover, due to the significant risks of such a major surgical intervention, it is difficult to reduce the morbidity associated with this treatment option. Therefore, this approach for the treatment of lymphedema involves high costs as well as significant strain, hassle and risks for the patient.

In the literature, avascular transplantation of autologous lymph node fragments has been reported (Sommer et al., 2012; Pabst et al., 1988). However, the handling and fixation of small lymph node fragments in the target tissue (typically by suture) is difficult and time-consuming. Moreover, the size of the lymph nodes obtained by such techniques is rather small, there is little influence on the size and shape of the resulting lymph nodes and the success rate is dissatisfactory.

SUMMARY OF THE INVENTION

Thus, there is a need in the art for improved ways to treat lymphedema, especially chronic lymphedema. In particular, there is a need in the art for ways to treat (chronic) lymphedema that overcome the above-described drawbacks. Thus, there is a need in the art for ways to treat (chronic) lymphedema that result in long-lasting effects and at the same time allow for shorter times of surgical intervention and/or save costs and/or are more convenient and/or less risky for the patient treated and/or provide more pronounced improvements of the symptoms of lymphedema and/or provide improvements of the symptoms of lymphedema more rapidly. It is the object of the present invention to meet such needs.

These objects are solved by the below-described aspects of the present invention, in particular by an implant according to claim 1 and by a method of manufacturing such an implant according to claim 2. Preferable embodiments are defined in the dependent claims.

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Moreover, the following embodiments can, wherever this does not lead to logical contradictions, be combined with each other without restrictions. Hence, the present disclosure encompasses, even where not explicitly spelled out in the following, any feasible combination of the embodiments described below. Furthermore, embodiments relating to one aspect of the present invention can, wherever this does not lead to logical contradictions, be combined with another aspect of the present invention without restrictions.

In a first aspect, the present invention relates to an implant, said implant comprising
a biodegradable scaffold and
lymph node fragments immobilized in and/or on said biodegradable scaffold.

Such an implant may be prepared as follows:
In a first step, a lymph node is obtained from the body of a patient suffering from lymphedema.

The lymph node can be acquired by standard surgical procedures known to the skilled person, such as by biopsy.

As the skilled person will appreciate, the lymph node obtained should optimally be a healthy lymph node, i.e. a lymph node that is fully functional (and thus capable of fulfilling its function in the removal of interstitial fluid from a tissue). This can be made sure by using a lymph node from a body area that is not affected by lymphedema.

Advantageously, the healthy lymph node is obtained from an area of the body which has a high density of lymph nodes, such that removal of said lymph node does not by itself give rise to lymphedema formation at the body area from which said lymph node is removed. Particularly suitable body areas for obtaining said lymph node are therefore, for example, the axilla or the groin.

The lymph node is then mechanically divided into fragments. This may for example be achieved by cutting the lymph node with a scalpel into several slices. However, lymph node fragments of other shapes than slices and fragments prepared by other ways may be used in the present invention, as well.

Subsequently, the lymph node fragments are immobilized in and/or on a biodegradable scaffold, thus providing an implant according to the invention. As the skilled person will appreciate, all components of the implant have to be compatible with in vivo use in the body of a patient, i.e. they should e.g. not cause adverse reactions like a rejection reaction of the patient's immune system or have poisonous effects.

Immobilization of said lymph node fragments to (i.e. in and/or on) the biodegradable scaffold may be achieved by gluing the lymph node fragments with fibrin or hyaluronic acid to the biodegradable scaffold, wherein said lymph node fragments may either be partially covered with fibrin/hyaluronic acid or fully embedded in fibrin/hyaluronic acid. Alternatively, the lymph node fragments may be embedded in a matrix of Matrigel™ (a gelatinous protein mixture secreted by Engelbreth-Holm-Swarm (EHS) mouse sarcoma cells produced and marketed by Corning Life Sciences) or a similar proteinaceous matrix that is filled into a lumen within the biodegradable scaffold. As a further alternative, the biodegradable scaffold may comprise cavities into which the lymph node fragments are wedged. This is particularly suitable if the biodegradable scaffold comprises or is made of a flexible or elastic material.

As material for the biodegradable scaffold, polycaprolactone (PCL), poly(1,3-trimethylene carbonate), polylactide, polyglycolide, poly(ester amide), poly(ethylene glycol)/poly(butylene terephthalate), poly(glycerol sebacate), poly(1,8-octanediol-co-citric acid), poly(1,10-decanediol-co-D,L-lactic acid), poly(diol citrate), poly(glycolide-co-caprolactone), poly(1,3-trimethylene carbonate-co-lactide), poly(1,3-trimethylene carbonate-co-caprolactone), polyurethane, or a copolymer of at least two of these materials may be used. As a further alternative, a matrix extracted from algae or collagen may be used.

The biodegradable scaffold may have a bar-and-strut structure formed by fused deposition modeling (FDM, which is synonymous with fused filament fabrication (FFF)), by laser sintering or by stereolithography, with a suitable material. Alternatively, the scaffold may be formed by melt electrospinning on a rotating cylindrical collector. If a computer/software-controlled manufacturing process is applied, design, architecture and mechanical properties of the scaffold can be adapted as required.

The biodegradable scaffold with lymph node fragments immobilized therein and/or thereon can be transplanted into the body of said patient suffering from lymphedema at the area affected by lymphedema (if the lymph node fragments were obtained from the patient suffering from lymphedema himself/herself, the implant will be re-transplanted to said patient at the body region affected by lymphedema, i.e. the lymph node fragments will be autotransplanted). Advantageously, the implant is placed close to a blood vessel, preferably an artery (i.e. a blood vessel that carries blood away from the heart). This ensures optimal supply of oxygen and nutrients to the lymph node fragments immobilized in and/or on the biodegradable scaffold by diffusion from the blood vessel to the lymph node fragments and ensures survival of the tissue of the lymph node fragments.

As the skilled person will appreciate, there may be holes and/or pores within the structure of the biodegradable scaffold, which upon implantation can rapidly be colonized by lymph node tissue, lymph vessels and/or blood vessels. Moreover, since the scaffold is made of a biodegradable material, the scaffold will be gradually degraded upon implantation, thus leaving additional space that can be invaded by lymph node tissue, lymph vessels and/or blood vessels.

The lymph node tissue of the implant secretes growth factors, like VEGF-C, which induces rapid formation of new lymph vessels to connect the lymph node tissue of the fragments immobilized in and/or on the implant to the lymph system in the surrounding tissue (lymphangiogenesis). At the same time, connecting blood vessels sprout from the surrounding tissue, in particular from the blood vessel close to which the implant was placed, into the lymph node tissue of the implant. Within a few weeks to months, the lymph node tissue of the individual fragments grows together and reorganizes to jointly foul' a mature, fully functional lymph node.

As the skilled person will appreciate, obtaining the lymph node from which the fragments are to be prepared, generating the lymph node fragments, immobilizing said fragments in and/or on the biodegradable scaffold and implanting the scaffold with immobilized lymph node fragments should be performed quickly in the interest of minimizing tissue necrosis. Moreover, since the implant is intended for implantation into the body of a patient, all components used should be sterile and all steps for preparing the implant should be carried out under sterile conditions.

The inventors have surprisingly found that the use of multiple lymph node fragments immobilized in and/or on a biodegradable scaffold results in major advantages.

Compared to the transplantation of a complete lymph node without microsurgically connecting it to a blood vessel, tissue necrosis upon implantation/transplantation is significantly reduced and the time span and success rate for regeneration of a fully functional lymph node is shortened. Without wishing to be bound by theory, the transplantation of multiple smaller fragments of lymph node tissue may increase the surface area through which oxygen and nutrients are delivered by diffusion. Moreover, since the fragments immobilized in and/or on the implant are smaller than a complete lymph node, the distance to reach the cells at the core of each fragment is much smaller than in the case of a whole lymph node. Thus, the supply of oxygen and nutrients to the transplanted lymph node tissue in the absence of a microsurgically connected blood vessel is improved. In addition, since the preparation of lymph node fragments results in tissue injury, increased levels of growth factors are secreted by the fragments, thus increasing the rate of angiogenesis and lymphangiogenesis. Accordingly, the connection of the implanted lymph node tissue to the surrounding blood and lymph vessels is improved.

Compared to the transplantation of an individual lymph node fragment, the use of multiple fragments in close spatial arrangement to each other allows faster regeneration of a fully functional lymph node of appropriate size, permits for the formation of larger and thus more effective lymph nodes and results in higher success rates for lymph node formation/regeneration. Moreover, since the implant according to the invention includes multiple fragments, higher levels of growth factors are secreted than by a single fragment, resulting in an increased rate of angiogenesis and lymphangiogenesis.

The inventors have surprisingly found that, due to its size, the biodegradable scaffold with immobilized lymph node fragments is held in place at its specific site of transplantation (e.g. close to a blood vessel) much more reliably than a small lymph node fragment or multiple individual lymph node fragments that are not attached to a scaffold. Thus, the implant according to the invention does not require mechanical coupling to the surrounding tissue e.g. by surgical suture. Moreover, immobilization in and/or on the biodegradable scaffold allows for a highly defined spatial arrangement of the individual lymph node fragments with respect to each other. For example, the lymph node fragments can be placed close to each other for efficient regeneration of a complete, fully functional lymph node, while at the same time leaving each lymph node fragment space for efficient supply of oxygen and nutrients by diffusion. Transplantation of multiple small lymph node fragments in such a defined spatial arrangement at a specific site of transplantation close to a blood vessel could hardly be successful through fixation with surgical suture as it would be required in the absence of a scaffold. By using appropriately shaped scaffolds, it is even possible to specifically design the lymph node to be generated to a desired shape. At the same time, the implant according to the invention does not require a second surgical operation later on to remove the scaffold of the implant, since the scaffold is biodegradable and hence completely degraded and resorbed over time.

Since the implantation does not require any complicated surgical steps (in contrast to an operation involving the microsurgical connection of blood vessels), this surgical intervention may be carried out in a rather undemanding operation within an hour under local anesthesia. Due to the lower technical hurdles, shorter operation times and subsequent shorter hospitalization of the patient, a significant reduction in cost, strain and hassle for the patient and patient morbidity is achieved.

In some embodiments, said implant is an implant for the treatment of lymphedema, preferably of chronic lymphedema.

In some embodiments, said implant is for implantation into a patient suffering from lymphedema, preferably from acute or chronic lymphedema.

In some embodiments, said implant is an implant for the formation and/or regeneration of a lymph node, preferably for the formation and/or regeneration of a lymph node in the body of a patient in need thereof. Preferably, said patient is suffering from lymphedema, more preferably from chronic lymphedema.

Preferably, said patient (i.e. the patient suffering from lymphedema referred to above/the patient in need of formation and/or regeneration of a lymph node referred to above) is a human.

In some embodiments, said lymph node fragments are fragments of a human lymph node.

In some embodiments, said lymph node fragments are fragments of a lymph node obtained from said patient (i.e. the patient suffering from lymphedema referred to above/the patient in need of formation and/or regeneration of a lymph node referred to above). Since the lymph node fragments originate from a lymph node that was acquired from the same patient, no rejection reaction of the patient's immune system against the tissue/cells included in the implant occurs. Moreover, since procurement of the lymph node, preparation of the fragments from the lymph node, preparation of the implant and the implantation step can be done during a single surgical intervention, additional complications arising from national transplantation law can be avoided in many countries.

In some embodiments, said lymph node fragments are fragments of a healthy lymph node. In some embodiments, said lymph node fragments are obtained from a lymph node capable of fulfilling the regular function of a lymph node in the removal of interstitial fluid from tissue.

In some embodiments, said lymph node fragments are fragments of a lymph node obtained from a body part which does not suffer from lymphedema.

In some embodiments, said lymph node fragments are fragments of a lymph node obtained by biopsy.

In some embodiments, said lymph node fragments are fragments of an axillary or inguinal lymph node.

In some embodiments, said lymph node fragments are slices of a lymph node with a thickness of not more than 2 mm, preferably not more than 1 mm. Such slices may be prepared by cutting a lymph node into slices with a surgical blade. Since the slices are thin, good supply of the lymph node tissue of said slices with oxygen and nutrients by diffusion is ensured.

In some embodiments, said lymph node fragments are pieces with a diameter of not more than 3 mm, preferably not more than 2 mm. By using such small fragments, optimal supply of the lymph node tissue of said fragments with oxygen and nutrients by diffusion can be ensured.

In some embodiments, said lymph node fragments are lymph node fragments immobilized in and/or on said biodegradable scaffold in a spatial arrangement such that said lymph node fragments are spaced from each other at a distance just sufficient to allow blood to enter into the space between said lymph node fragments. This has the advantage that diffusion of oxygen and nutrients into the lymph node fragments is possible from various sides of the lymph node fragments, while the individual lymph node fragments are still close enough to each other to facilitate coalescence of the individual lymph node fragments into one complete, functional lymph node.

In some embodiments, said biodegradable scaffold comprises or is made of flexible or elastic material.

In some embodiments, said biodegradable scaffold is made from a polymer, more preferably from a synthetic polymer.

In some embodiments, said biodegradable scaffold is made from polycaprolactone, polyglycolide, polylactide, poly(1,3-trimethylene carbonate) or a copolymer of polycaprolactone and either poly-trimethylene carbonate or polylactide or a copolymer of polycaprolactone, polylactide and polyglycolide. Preferably, said biodegradable scaffold is made from polycaprolactone.

In some embodiments, said biodegradable scaffold comprises holes and/or pores which reach through the three-dimensional structure of said biodegradable scaffold. Preferably, said holes and/or pores have a diameter in the range of from 20 µm to 2 mm, more preferably in the range of from 20 µm to 200 µm or, alternatively, in the range of from 1 mm to 2 mm. Such a configuration of the biodegradable scaffold allows oxygen or cell nutrients to freely diffuse through the scaffold. This is particularly advantageous in a spatial arrangement in which the scaffold or a part of the scaffold ends up between the lymph node fragments and the blood vessel (as e.g. shown in the examples of FIG. 2C or FIG. 4C). Moreover, larger holes and/or pores may allow to immobilize lymph node fragments by wedging them into cavities provided by the holes and/or pores.

In some embodiments, said biodegradable scaffold is a hollow three-dimensional object (i.e. it is e.g. a hollow cylinder, a hollow cuboid, a hollow triangular prism or a hollow cone). Preferably, said lymph node fragments are immobilized inside (i.e. within the lumen) and/or on the inner surface (i.e. on the surface delimiting the inside lumen) of said hollow three-dimensional object. This has the advantage that through the shape and size of the lumen of said biodegradable scaffold, full control can be exerted over the size and three-dimensional shape of the lymph node to be formed/regenerated (in particular, if a biodegradable scaffold made from a material that is degraded only slowly in the body is used). Alternatively, said lymph node fragments are immobilized on the outer surface of said hollow three-dimensional object.

In some embodiments, said biodegradable scaffold has a tubular shape (i.e. the shape of a hollow cylinder; an example of a biodegradable scaffold with a tubular shape is shown in FIG. 2A). Preferably, said lymph node fragments are immobilized inside and/or on the inner surface of said biodegradable scaffold having a tubular shape (see FIG. 2B for an exemplary embodiment). This has the advantage that the size and three-dimensional shape of the lymph node to be formed/regenerated can be fully controlled by the shape and size of the lumen of said biodegradable scaffold having a tubular shape. Alternatively, said lymph node fragments are immobilized on the outer surface of said biodegradable scaffold having a tubular shape.

In some embodiments, said biodegradable scaffold has the shape of a tube with a longitudinal slit on one side (i.e. the scaffold has the shape of a hollow cylinder which is not completely closed, but has an elongated gap running parallel to its longitudinal axis in its wall; for an example of a biodegradable scaffold having the shape of a tube with a longitudinal slit on one side, see FIG. 3A). A tube of such a shape can be bent in such a way that the slit is widened to place the bent-open tube around another, preferably elongated, shape. Upon release, the bent-open scaffold will return to its (almost closed) tubular shape, in particular if the biodegradable scaffold comprises or is made from a flexible or elastic material. This way, the scaffold can be placed e.g. around a blood vessel (see FIG. 3C and FIG. 4C for examples). Preferably, said lymph node fragments are immobilized inside (i.e. within the lumen) and/or on the inner surface (i.e. on the surface delimiting the inside lumen) of said biodegradable scaffold having the shape of a tube with a longitudinal slit on one side (see e.g. FIG. 3C). This has the advantage that the lymph node fragments are stably held in place in very close proximity to the nourishing blood vessel, while the shape and size of the lymph node to be formed/regenerated can be fully controlled by the shape and size of the lumen of the tube with a longitudinal slit on one side. Alternatively, said lymph node fragments are immobilized on the outer surface of said biodegradable scaffold having the shape of a tube with a longitudinal slit on one side (see e.g. FIG. 4C). This has the advantage that the lymph node fragments are stably held in place in proximity to the nourishing blood vessel, while leaving the lymph node to be formed/regenerated some freedom with respect to the three-dimensional shape that it will adopt.

By pursuing an integrated approach which links medical imaging technology with Computer Aided Design and Computer Aided Manufacturing (CAD/CAM), it is possible to specifically design customized three-dimensional scaffold structures for implants to fit a certain target location (such as a scaffold in the shape of a tube with a longitudinal slit on one side which specifically fits a blood vessel of a certain thickness).

In some embodiments, said implant comprises from 2 up to 10, preferably from 3 up to 6, more preferably from 4 up to 5, lymph node fragments immobilized in and/or on said biodegradable scaffold.

In some embodiments, said lymph node fragments are lymph node fragments immobilized in and/or on said biodegradable scaffold with fibrin (i.e. the lymph node fragments are lymph node fragments glued to said biodegradable scaffold with fibrin). The use of fibrin has the advantage that fibrin stimulates cells to release growth factors which further support efficient regeneration of a functional lymph node from the immobilized lymph node fragments. The fibrin is degraded in the body within several days. However, in the meanwhile the lymph node fragments have already formed a stable attachment to the biodegradable scaffold and surrounding tissue through cell/tissue adhesion molecules.

In some embodiments, said lymph node fragments are lymph node fragments immobilized in and/or on said biodegradable scaffold with hyaluronic acid (i.e. the lymph node fragments are lymph node fragments glued to said biodegradable scaffold with hyaluronic acid). Hyaluronic acid is a lymphangiogenesis inducer. Hence, the use of hyaluronic acid has the advantage that the rate of lymphangiogenesis is further increased.

In some embodiments, said lymph node fragments are lymph node fragments immobilized in and/or on said biodegradable scaffold by being embedded in a proteinaceous matrix, preferably a proteinacous matrix formed from a protein mixture secreted by Engelbreth-Holm-Swarm (EHS) mouse sarcoma cells, more preferably by embedding said lymph node fragments in a matrix formed from Matrigel™ (Corning Life Sciences). This has the advantage that the lymph node fragments can be arranged in a three-dimensional spatial arrangement, in particular if the lymph node fragments embedded in said matrix are filled into the lumen of a hollow geometric shape formed from said biodegradable scaffold, such as into a biodegradable scaffold having a tubular shape. At the same time, free diffusion of oxygen and nutrients to the lymph node fragments is only marginally reduced by this type of matrix, and the matrix is degraded by proteinases and replaced by cell adhesion molecules and/or connective tissue within a few days upon implantation. As the skilled person will appreciate, immobilization of lymph node fragments on said biodegradable scaffold by embedding said lymph node fragments in a proteinaceous matrix can be accomplished by using a biodegradable scaffold that has the shape of a hollow geometric shape (such as a biodegradable scaffold with a tubular shape) and placing the proteinaceous matrix with lymph node fragments distributed therein into the lumen of said hollow geometric shape.

In some embodiments, said lymph node fragments are lymph node fragments immobilized in and/or on said biodegradable scaffold by having been wedged into cavities present within said biodegradable scaffold. This has the advantage that the immobilization procedure is particularly fast, thus reducing tissue necrosis, and does not require further reagents.

In a second aspect, the present invention relates to a method of manufacturing an implant, said method comprising the steps of
providing a biodegradable scaffold and
immobilizing lymph node fragments in and/or on said biodegradable scaffold.

Preferably, said implant, said biodegradable scaffold and/or said lymph node fragments are as defined in any of the embodiments above (or as defined by a combination of any of the embodiments described above).

Preferably, said method comprises only steps carried out in vitro.

In some embodiments, said immobilizing lymph node fragments in and/or on said biodegradable scaffold comprises or consists of immobilizing 2 to 10, preferably 3 to 6, more preferably 4 to 5, lymph node fragments in and/or on said biodegradable implant.

In some embodiments, said immobilizing lymph node fragments in and/or on said biodegradable scaffold comprises or consists of immobilizing said lymph node fragments in and/or on said biodegradable scaffold in a spatial arrangement such that said lymph node fragments are spaced from each other at a distance just sufficient to allow blood to enter into the space between said lymph node fragments.

In some embodiments, said immobilizing lymph node fragments in and/or on said biodegradable scaffold comprises or consists of immobilizing said lymph node fragments in and/or on said biodegradable scaffold with fibrin (i.e. gluing the lymph node fragments to said biodegradable scaffold with fibrin).

In some embodiments, said immobilizing lymph node fragments in and/or on said biodegradable scaffold comprises or consists of immobilizing said lymph node fragments in and/or on said biodegradable scaffold with hyaluronic acid (i.e. gluing the lymph node fragments to said biodegradable scaffold with hyaluronic acid).

In some embodiments, said immobilizing lymph node fragments in and/or on said biodegradable scaffold comprises or consists of embedding said lymph node fragments in a proteinaceous matrix, preferably a proteinacous matrix formed from a protein mixture secreted by Engelbreth-Holm-Swarm (EHS) mouse sarcoma cells, more preferably by embedding said lymph node fragments in a matrix formed from Matrigel™ (Corning Life Sciences).

In some embodiments, said immobilizing lymph node fragments in and/or on said biodegradable scaffold comprises or consists of immobilizing said lymph node fragments in and/or on said biodegradable scaffold by wedging said lymph node fragments into cavities present within said biodegradable scaffold.

In a third aspect, the present invention relates to a method of treating lymphedema, preferably of treating chronic lymphedema, in the body of a patient, said method comprising the step of implanting into said body of said patient at the body part affected by said (chronic) lymphedema an implant comprising a biodegradable scaffold and lymph node fragments immobilized in and/or on said biodegradable scaffold.

Preferably, said patient, said implant, said biodegradable scaffold and said lymph node fragments are as defined in any of the embodiments above.

In some embodiments said method of treating (chronic) lymphedema in the body of a patient further comprises, previous to the step of implanting said implant, the steps of
removing from the body of said patient a lymph node,
preparing lymph node fragments from said lymph node removed from the body of said patient,
immobilizing said lymph node fragments in and/or on a biodegradable scaffold,
to obtain said implant comprising a biodegradable scaffold and lymph node fragments immobilized in and/or on said biodegradable scaffold.

An "implant", as used herein, is a medical device manufactured to replace a missing or damaged biological structure, to support a damaged biological structure, and/or to enhance an existing biological structure. In particular, as used herein, an implant is an implant for the reconstruction of body tissue and/or the restoration of the function of a tissue or organ, preferably for the reconstruction of a lymph node and/or the restoration of lymph node function in the removal of interstitial fluid from a body tissue.

If the present application indicates that the lymph node fragments are "glued" to the biodegradable scaffold with fibrin or hyaluronic acid, this also includes a situation where said lymph node fragments are glued to said biodegradable scaffold in a way such that some or all of said lymph node fragments are fully embedded in said fibrin or hyaluronic acid.

As used herein, the term "in vitro" means occurring outside of a living organism. The term in vitro can describe processes/conditions occurring within a cell culture system or in tissue removed from the living organism from which it originates. In contrast to "in vitro", the term "in vivo" means occurring within a living organism.

As used herein, a "patient suffering from lymphedema" is a patient exhibiting swelling of a body region due to an abnormal collection of fluid in the interstitium resulting from impaired lymphatic drainage. A "body part suffering from lymphedema" is a body part exhibiting swelling due to an abnormal collection of fluid in the interstitium resulting from impaired lymphatic drainage.

The present invention refers to a lymph node as a "healthy lymph node", if said lymph node is capable of fulfilling the functions that a lymph node normally fulfills in the body without restrictions, in particular if said lymph node is capable of mediating removal of interstitial fluid from the tissue surrounding said lymph node at a rate as typically observed for lymph nodes. Such a lymph node can be recognized by the fact that the body area or tissue where said lymph node is located is not affected by lymphedema and/or abnormal accumulation of interstitial fluid. As used herein, a lymph node is said to be "capable of fulfilling the regular function of a lymph node in the removal of interstitial fluid from tissue", if the body area or tissue where said lymph node is located is not affected by lymphedema and/or abnormal accumulation of interstitial fluid.

As used herein, a biodegradable scaffold that "is a hollow three-dimensional object" is a biodegradable scaffold that forms the outer walls of a three-dimensional object, while there is no biodegradable scaffold present in the inner area embraced by said outer walls, resulting in the formation of a lumen enveloped by walls made from said biodegradable scaffold. Examples of hollow three-dimensional objects are a hollow cylinder, a hollow cuboid, a hollow triangular prism or a hollow cone.

BRIEF DESCRIPTION OF THE FIGURES

In the following, reference is made to the figures, wherein.

All methods mentioned in the figure descriptions above were carried out as described in detail in the Examples.

DETAILED DESCRIPTION OF EXEMPLARY EMBODIMENTS

For the purpose of promoting an understanding of the principles of the invention, reference will now be made to the preferred embodiments and specific language will be used to describe the same. It will nevertheless be understood that no limitation of the scope of the invention is intended thereby, such alterations and further modifications in the device and methods and such further applications of the principles of the invention as illustrated therein being contemplated as would normally occur now or in the future to one skilled in the art to which the invention relates.

Moreover, it is to be understood that features and advantages described with regard to one aspect of the invention may also be implied by other aspects of the invention.

Figure 1:
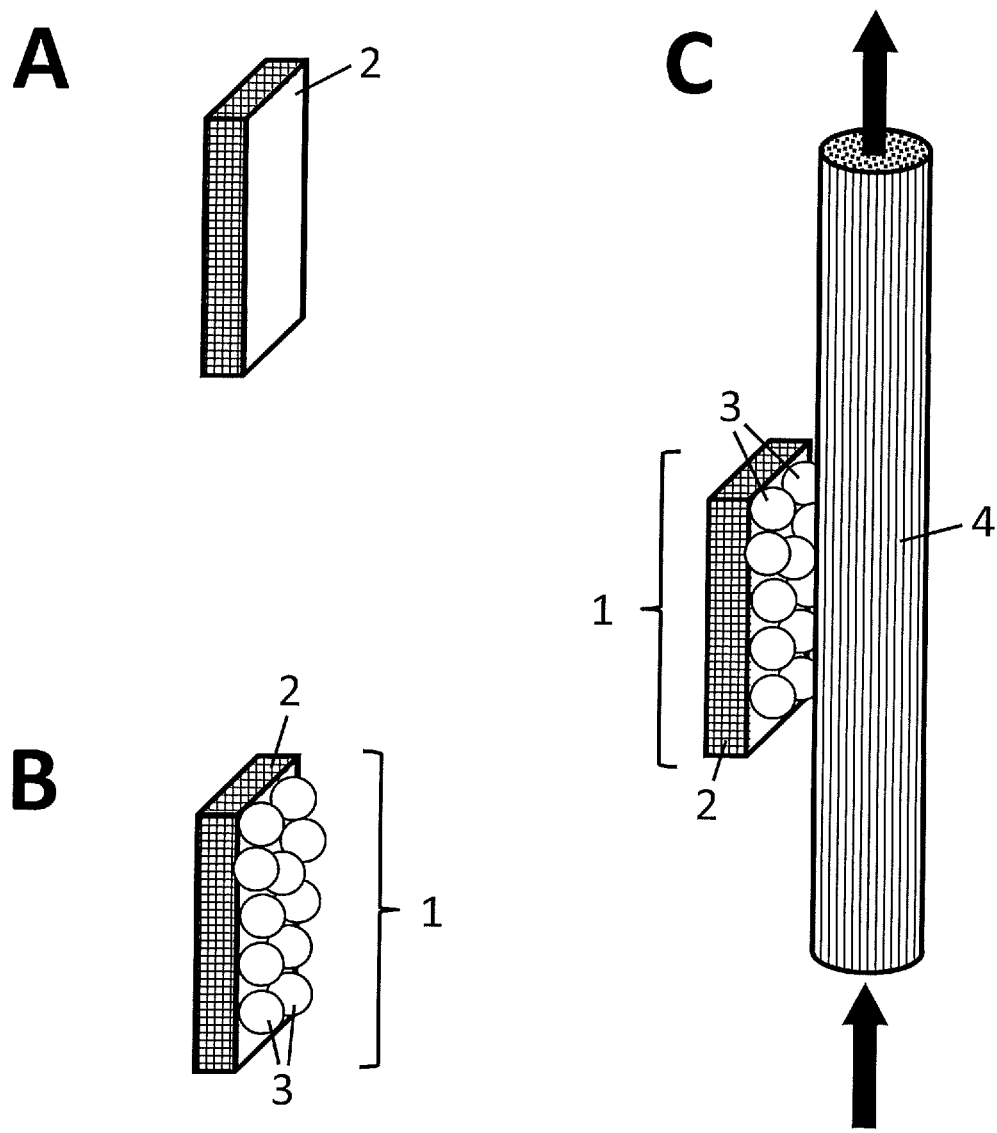
FIG. 1 shows an exemplary embodiment of the present invention wherein the biodegradable scaffold has the shape of a sheet or flat cuboid.
(A) Example of a biodegradable scaffold in the shape of a sheet or flat cuboid.
(B) Exemplary embodiment of an implant according to the present invention comprising a biodegradable scaffold having the shape of a sheet or flat cuboid.
(C) Example of such an implant placed in proximity to a blood vessel.

FIG. 1 shows an exemplary embodiment of an implant according to the present invention and its possible placement relative to a blood vessel. In this embodiment, the biodegradable scaffold 2 of the implant 1 has the shape of a sheet or flat cuboid (FIG. 1 A). Lymph node fragments 3 are immobilized on the surface of the biodegradable scaffold 2, for example by gluing them with fibrin to the biodegradable scaffold, resulting in an implant 1 according to the invention (FIG. 1 B). The implant 1 according to the invention can be placed in the proximity of a blood vessel 4 (FIG. 1 C; blood flow shown by arrows). Due to the proximity to the blood vessel 4, the lymph node fragments 3 are supplied efficiently with oxygen and nutrients. Thus, within a few weeks to months, the individual lymph node fragments 3 grow together, develop blood vessels connecting them to the blood circulation of the body and lymph vessels linking them to the lymph system, and reorganize to form/regenerate a fully functional lymph node that is capable of removing interstitial fluid from the tissue surrounding it.

Figure 2:
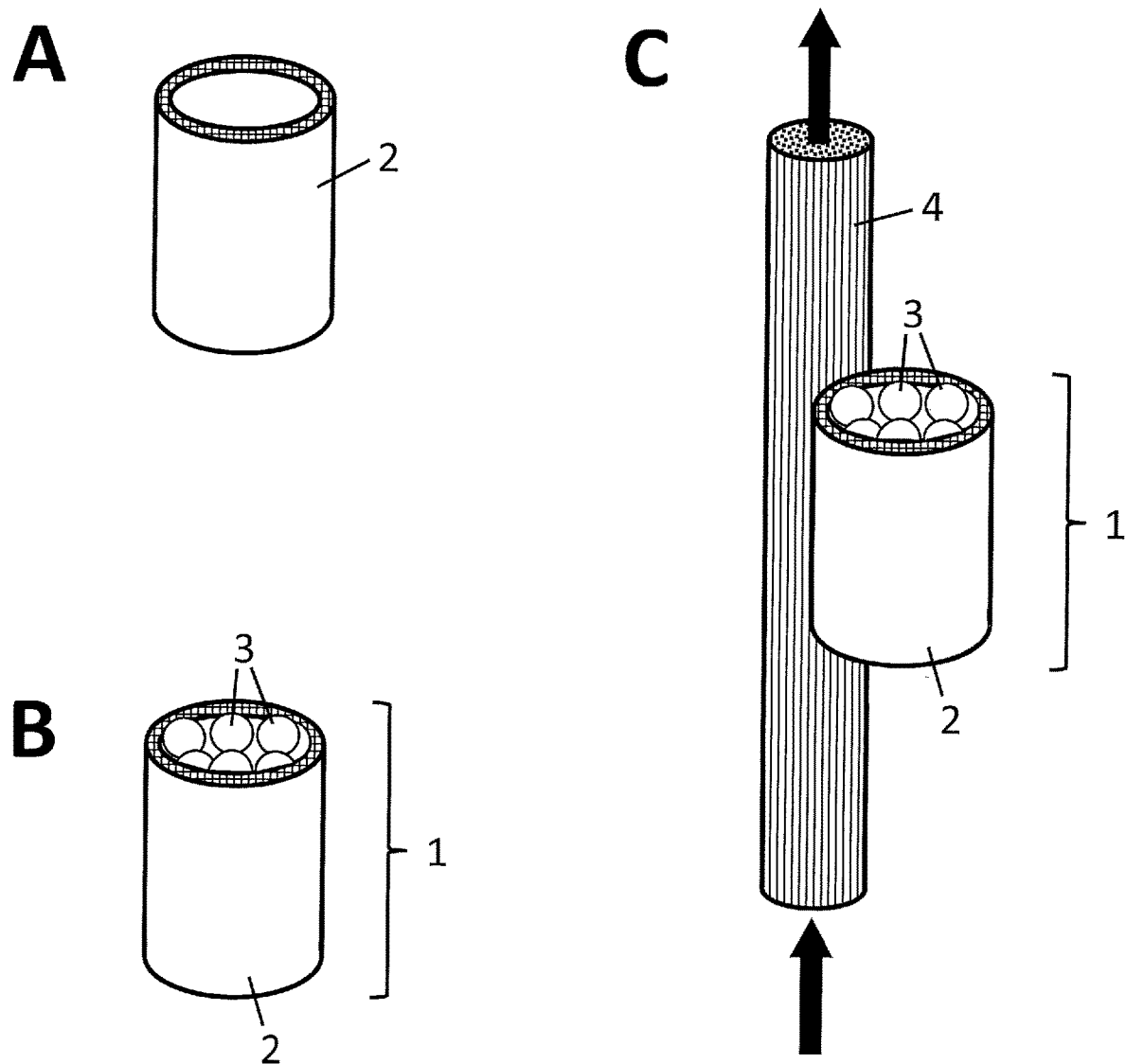
FIG. 2 shows an exemplary embodiment of the present invention wherein the biodegradable scaffold has a tubular shape.
(A) Example of a biodegradable scaffold with a tubular shape.
(B) Exemplary embodiment of an implant according to the present invention comprising a biodegradable scaffold having a tubular shape, wherein the lymph node fragments are immobilized within the lumen of said tubular shape.
(C) Example of such an implant placed in proximity to a blood vessel.

FIG. 2 shows another exemplary embodiment of an implant according to the present invention and its possible placement relative to a blood vessel. In this embodiment, the biodegradable scaffold 2 of the implant 1 has a tubular shape (FIG. 2 A). Lymph node fragments 3 are immobilized within the lumen of the tubularly shaped biodegradable scaffold 2, for example by embedding the lymph node fragments 3 in fibrin within the lumen of the biodegradable scaffold 2, resulting in an implant 1 according to the invention (FIG. 2 B). The implant 1 according to the invention can be placed in the proximity of a blood vessel 4 (FIG. 2 C). Due to the proximity to the blood vessel 4, the lymph node fragments 3 are supplied efficiently with oxygen and nutrients, allowing for efficient formation/regeneration of a fully functional lymph node. The size and three-dimensional shape of the lymph node to be formed/regenerated can be influenced by the shape and size of the lumen of said biodegradable scaffold 2 having a tubular shape.

Figure 3:
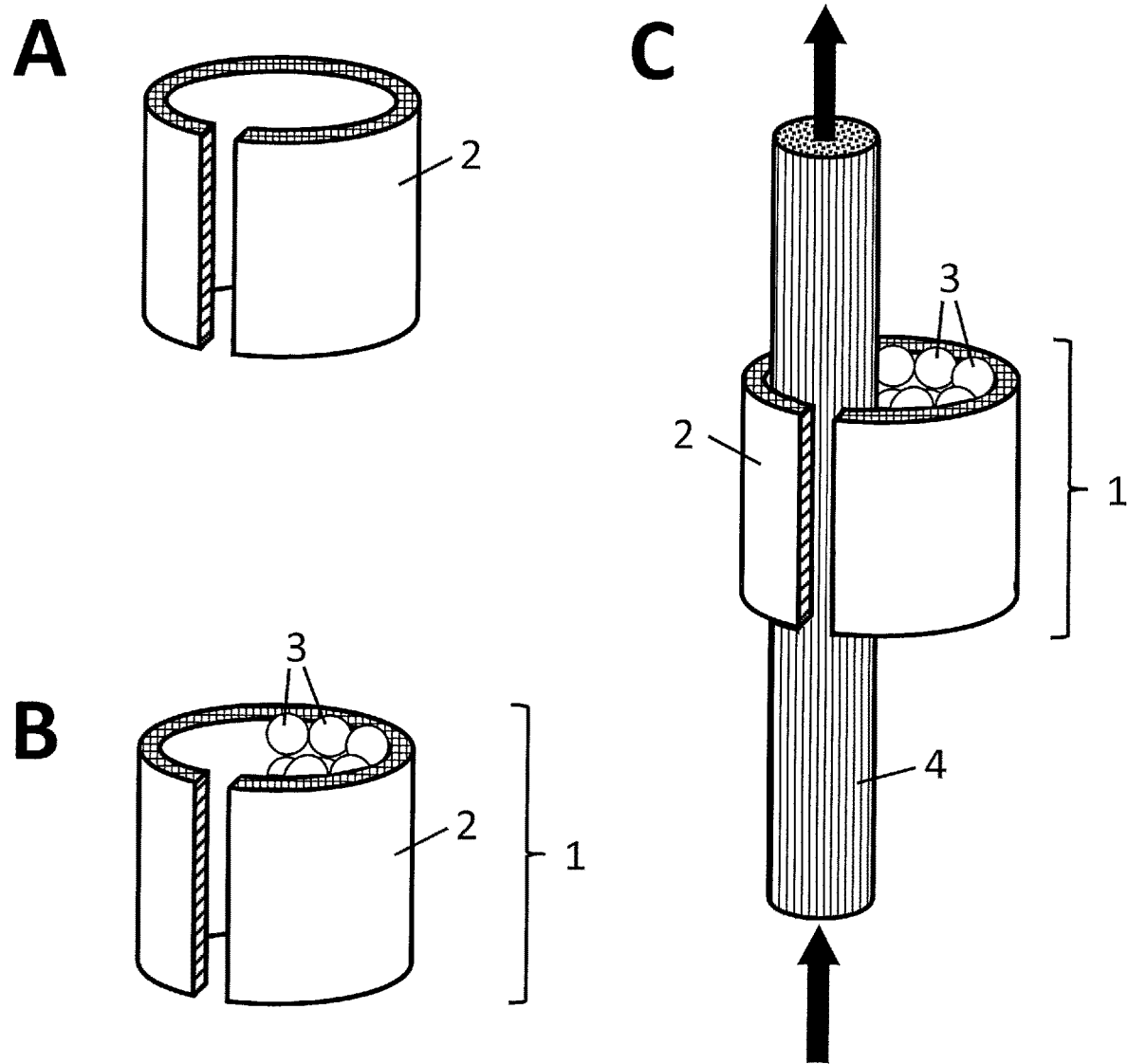
FIG. 3 shows an exemplary embodiment of the present invention wherein the biodegradable scaffold has the shape of a tube with a longitudinal slit on one side and wherein the lymph node fragments are immobilized at the inner face of the wall of said tube with a longitudinal slit on one side.
(A) Example of a biodegradable scaffold in the shape of a tube with a longitudinal slit on one side.
(B) Exemplary embodiment of an implant according to the present invention comprising a biodegradable scaffold in the shape of a tube with a longitudinal slit on one side, wherein the lymph node fragments are immobilized at the inner face of the wall of said tube with a longitudinal slit on one side.
(C) Example of such an implant placed around a blood vessel.

FIG. 3 shows another exemplary embodiment of an implant according to the present invention and its possible placement relative to a blood vessel. In this embodiment, the biodegradable scaffold 2 of the implant 1 has the shape of a tube with a longitudinal slit on one side (FIG. 3 A). Lymph node fragments 3 are immobilized at the inner face of the wall of the tube with a longitudinal slit on one side formed by the biodegradable scaffold 2, for example by gluing the lymph node fragments 3 with fibrin to the biodegradable scaffold 2, resulting in an implant 1 according to the invention (FIG. 3 B). The implant 1 according to the invention can be placed around a blood vessel 4 (FIG. 3 C). This ensures that the lymph node fragments 3 are stably held in place in very close proximity to the nourishing blood vessel 4, while the shape and size of the lymph node to be formed/regenerated is controlled by the shape and size of the lumen of the biodegradable scaffold 2.

Figure 4:
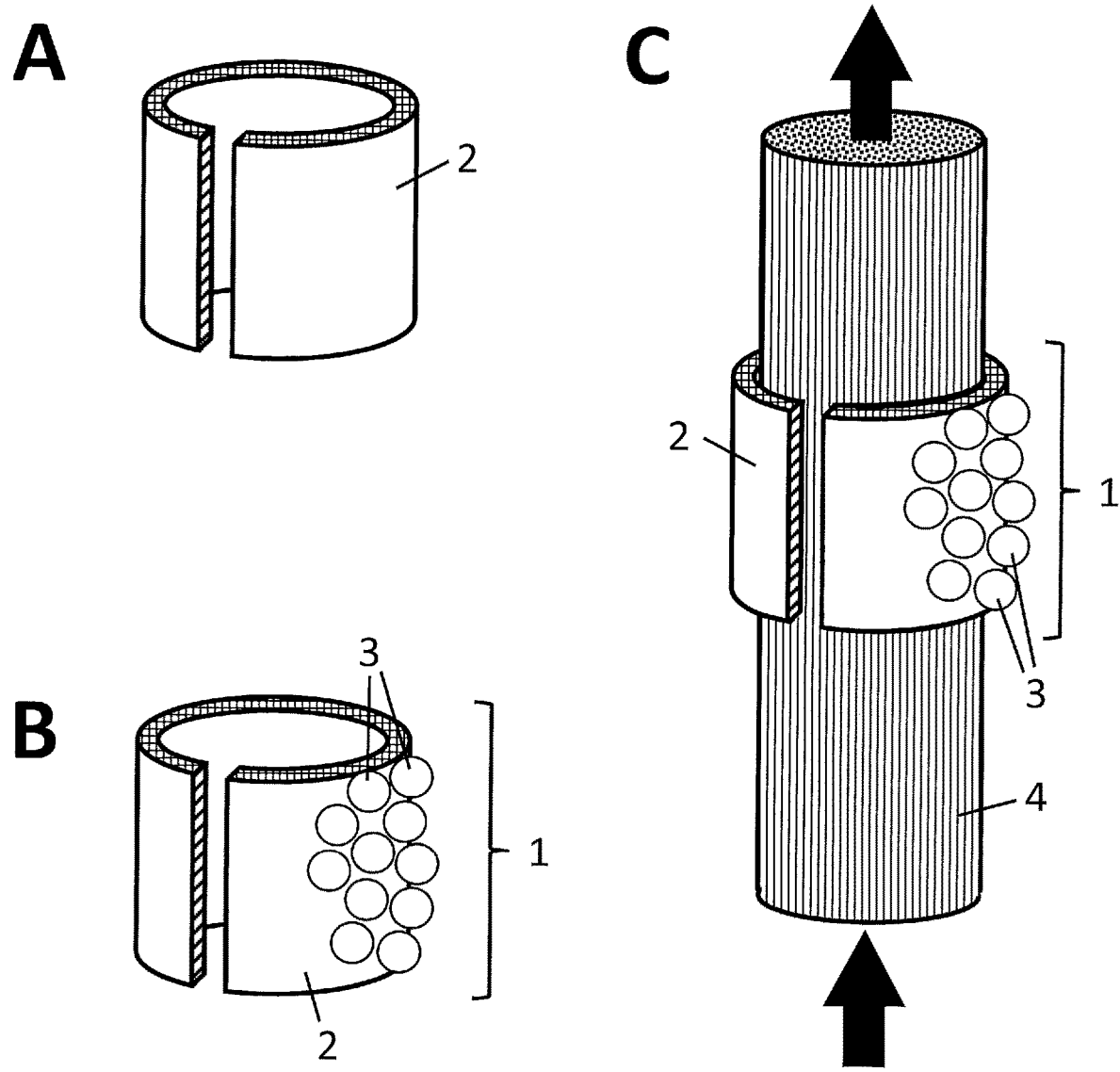
FIG. 4 shows an exemplary embodiment of the present invention wherein the biodegradable scaffold has the shape of a tube with a longitudinal slit on one side and wherein the lymph node fragments are immobilized at the outer face of the wall of said tube with a longitudinal slit on one side.
(A) Example of a biodegradable scaffold in the shape of a tube with a longitudinal slit on one side.
(B) Exemplary embodiment of an implant according to the present invention comprising a biodegradable scaffold in the shape of a tube with a longitudinal slit on one side, wherein the lymph node fragments are immobilized at the outer face of the wall of said tube with a longitudinal slit on one side.
(C) Example of such an implant placed around a blood vessel.

The embodiment depicted in FIG. 4 differs from that of FIG. 3 by the position of the immobilized lymph node fragments 3: While in the embodiment of FIG. 3 the lymph node fragments 3 are immobilized at the inner face of the wall of the tube with a longitudinal slit on one side, in the embodiment of FIG. 4 they are immobilized at the outer face. This ensures that the lymph node fragments 3 are stably held in place in proximity to the nourishing blood vessel 4, while leaving the lymph node to be formed/regenerated freedom with respect to the three-dimensional shape that it will adopt.

Not shown in FIGS. 1-4 is the structure of the biodegradable scaffold (holes, pores and/or cavities existing in the scaffold, e.g. between the bars and struts from which the biodegradable scaffold is formed). Typically, the biodegradable scaffold may not have a smooth surface. Moreover, while the lymph node fragments are indicated as spheres in FIGS. 1-4, it is to be understood that the lymph node fragments may have various other shapes or size and typically will be slices or rectangular blocks prepared by cutting a lymph node with a surgical blade.

As the skilled person will appreciate, various other shapes of the biodegradable scaffold, number, shapes and sizes of the immobilized lymph node fragments, ways to arrange or immobilize the lymph node fragments on the biodegradable scaffold, and spatial arrangements of the implant with respect to the blood vessel than those shown in the exemplary embodiments depicted in FIGS. 1-4 lie within the scope of the present invention, as well.

EXAMPLES

In the following, reference is made to the examples, which are given to illustrate, not to limit the present invention.

Example 1

Human lymph nodes were obtained by surgical removal and were mechanically broken up with a scalpel into lymph node fragments. The lymph node fragments were transferred into the lumen of a biodegradable polycaprolacton scaffold in the shape of a hollow cylinder (lymph node fragments obtained from one lymph node per scaffold) and fixed with fibrin glue. A growth of the lymphogenic cells in the 3D matrix structure takes place. DNA analysis reveals that the cells increasingly proliferate and spread throughout the scaffold. Subsequently, the biodegradable scaffold with the immobilized lymph node fragments was transplanted into one of the inguinal regions of immunodeficient nude mice, in close proximity to a blood vessel. A biodegradable scaffold with fibrin glue but no lymph node fragments was implanted into the other inguinal region of the immunodeficient mice so as to provide a control sample. The experiment was carried out with 7 mice.

Figure 5:
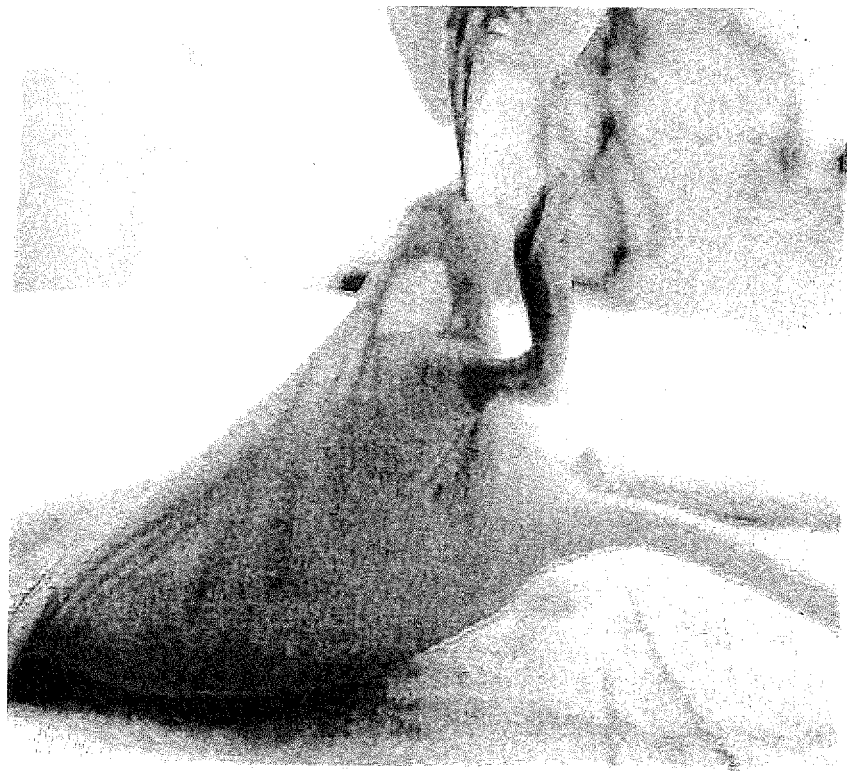
FIG. 5 shows a regenerated lymph node (bean-shaped structure held with forceps) during explantation carried out 8 weeks after implantation of a biodegradable scaffold with immobilized human lymph node fragments into the inguinal body region of a nude mouse.
Figure 6:
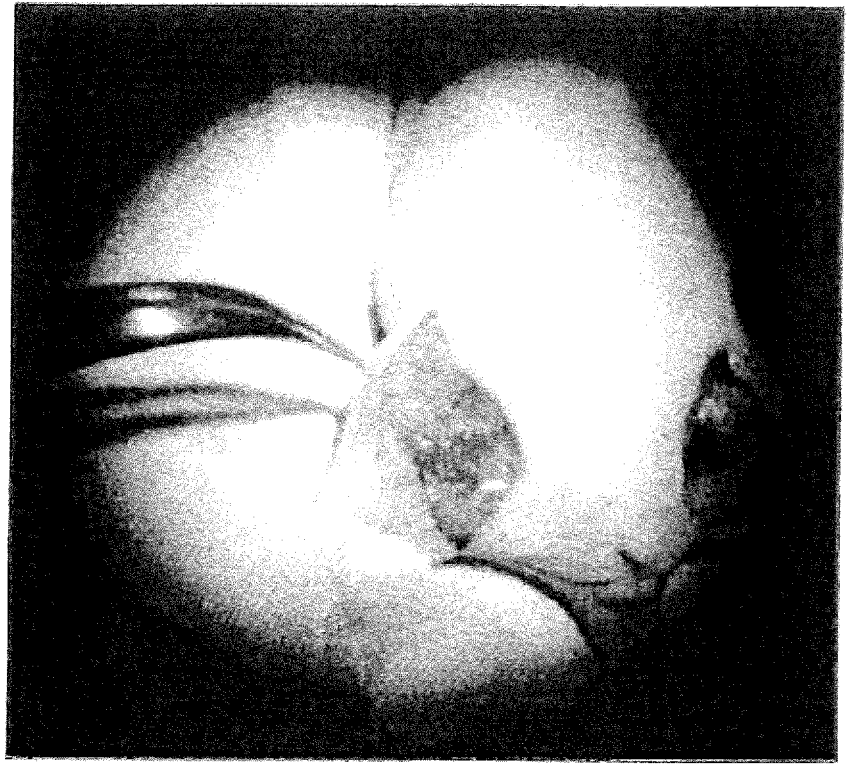
FIG. 6 is a photographic image obtained upon surgically opening the inguinal body region of a nude mouse where a polycaprolacton scaffold with immobilized human lymph node fragments had been implanted 8 weeks before. A full-grown lymph node of considerable size with very good vascularization and connection to the lymphatic system has developed, whereas the biodegradable scaffold has been degraded.

After 8 weeks, the site of transplantation was re-opened by surgery and in vivo imaging was carried out by injecting a contrast agent into the respective body region and examining the lymph nodes/lymph vessels in the living mice under anesthesia. It was observed that full-grown lymph nodes of considerable size had formed which were well vascularized and had developed new lymph vessels that connected them to the lymphatic system (FIGS. 5 and 6).

Figure 7:
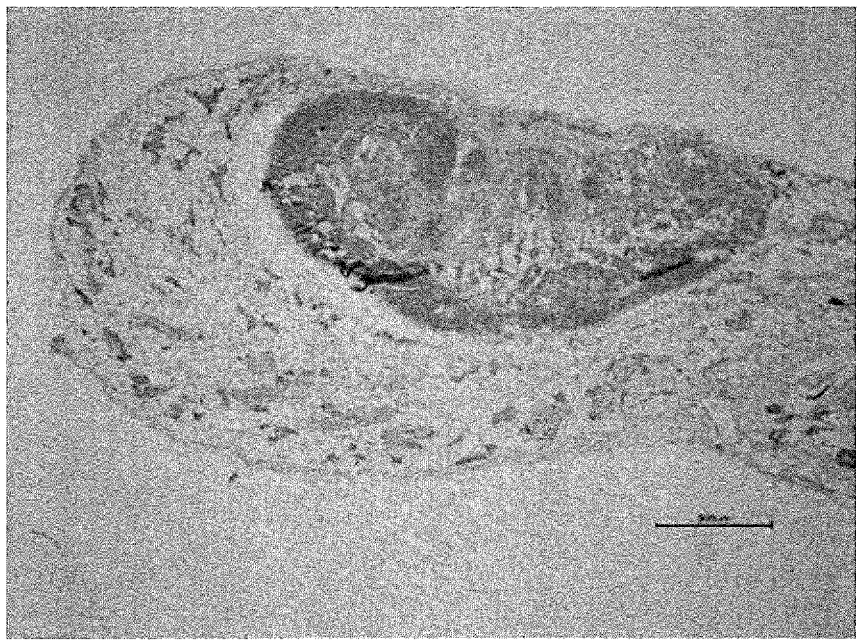
FIG. 7 shows a histological section of the inguinal body region of an immunodefficient mouse in which a biodegradable scaffold with immobilized human lymph node fragments had been implanted 16 weeks before. The formation of lymph vessels and lymphatic regeneration is observed.

After 16 weeks potential lymph vessels and high endothelial venules are also observed in the surrounding fatty tissues (FIG. 7). This provides evidence that the environment drains liquid into the regenerated lymph nodes and hence suggests functional activity thereof. Furthermore, the regenerated lymph nodes display similar structures to those characteristic of healthy lymph nodes, in particular lymph follicles, medulla and capsule.

Figure 8:
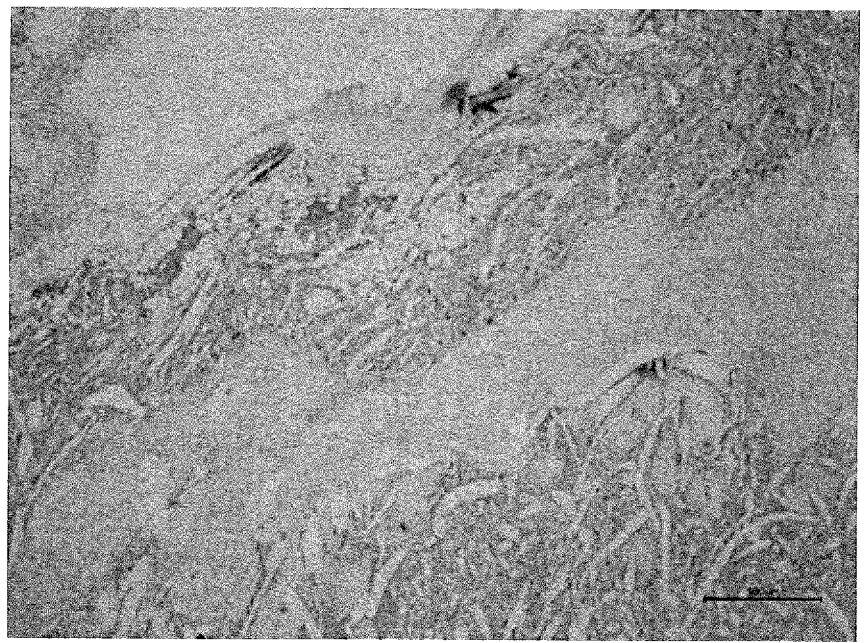
FIG. 8 shows a histological section of the inguinal body region of an immunodefficient mouse in which a biodegradable scaffold without any immobilized human lymph node fragments had been implanted 16 weeks before. Neither the formation of lymph vessels nor any significant signal of lymphatic regeneration is observed.

None of the reported features is significantly observed in the control sample group, that is, in the implants of the scaffold with fibrin glue but without any lymph node fragments (FIG. 8). This suggests that said features can be traced back to the implantation of the lymph node fragments.

Thus the lymph node fragments are observed to regenerate in mice and to display similar structures to those characteristic of healthy lymph nodes. They furthermore appear to retake their normal working function.

REFERENCES

Becker C, Assouad J, Riquet M, Hidden G. Postmastectomy lymphedema: long-term results following microsurgical lymph node transplantation. Ann Surg. (2006), 243(3): 313-315.

Pabst R, Rothkötter H J. Regeneration of autotransplanted lymph node fragments. Cell Tissue Res. (1988), 251(3): 597-601.

Sommer T, Buettner M, Bruns F, Breves G, Hadamitzky C, Pabst R. Improved regeneration of autologous transplanted lymph node fragments by VEGF-C treatment. Anat Rec (2012), 295(5):786-791.

The invention claimed is:

1. A method of manufacturing an implant for the formation and/or regeneration of a lymph node in a body of a patient in need thereof, the method comprising:
providing a biodegradable scaffold comprising a hollow three-dimensional object containing a lumen, and
immobilizing 2 to 10 lymph node fragments within the lumen;
wherein the lymph node fragments are arranged so as to facilitate coalescence into a single complete functional lymph node with a size and shape based on a size and shape of the lumen,
wherein the lynph node fragments include slices of a lymph node with a thickness not more than 2 mm, and/or pieces of a lymph node with a diameter not more than 3 mm.

2. The method according to claim 1, wherein immobilizing the lymph node fragments comprises immobilizing 3 to 6 lymph node fragments.

3. The method according to 1, wherein fibrin or hyaluronic acid is used for immobilizing the lymph node fragments.

4. The method of claim 1, wherein immobilizing the lymph node fragments includes embedding the lymph node fragments in a proteinaceous matrix.

5. The method of claim 1, wherein immobilizing the lymph node fragments includes wedging the lymph node fragments into cavities present within the hollow three-dimensional object.

6. The method according to claim 1, wherein the lymph node fragments include slices of a lymph node with a thickness not more than 1 mm, and/or pieces of a lymph node with a diameter not more than 2 mm.

7. The method according to claim 1, wherein the biodegradable scaffold has a tubular shape.

8. The method according to claim 7, wherein the tubular shape has a surface with a longitudinal slit.

9. The method according to claim 1, wherein said method comprises only step carried out in vitro.

10. The method according to claim 1, wherein the patient suffers from lymphedema.

11. The method according to claim 1, wherein the lymph node fragments are fragments of a lymph node obtained from the patient.

12. The method according to claim 1, wherein the lymph node fragments are fragments of a lymph node obtained from a body part without lymphedema.

13. The method according to claim 1, wherein the lymph node fragments are fragments of an axillary or inguinal lymph node.

14. A method of manufacturing an implanat for the formation and/or regeneration of a lymph node in a body of a patient in need thereof, the method comprising:
providing a biodegradable scaffold comprising a hollow three-dimensional object containing a lumen, and
immobilizing 2 to 10 lymph node fragments within the lumen;
wherein the lymph node fragments are arranged so as to facilitate coalescence into a single complete functional lymph node with a size and shape based on a size and shape of the lumen,
wherein the biodegradable scaffold comprises:
a) polycaprolactone, polyglycolide, polylactide, or poly (1,3-trimethylene carbonate), or
b) a copolymer of polycaprolactone and either polytrimethylene carbonate or polylactide, or
c) a copolymer of polycaprolactone, polylactide and polyglycolide.

15. The method of manufacturing an implant for the formation and/or generation of a lymph node in a body of a patient in need thereof, the method comprising:
immobilizing 2 to 10 lymph node fragments within the lumen;
providing a biodegradable scaffold comprising a hollow three-dimensional object containing a lumen, and
immobilizing 2 to 10 lymph node fragments within the lumen;
wherein the lymph node fragments are arranged so as to facilitate coalescence into a single complete functional lymph node with a size and shape based on a size and shape of the lumen,
wherein the biodegradable scaffold comprises holes and/or pores through the three-dimensional object, the holes and/or pores having a diameter of 20 μm to 2 mm.

16. An implant for the formation and/or regeneration of a lymph node in the body of a patient in need thereof, said implant comprising:
a biodegradable scaffold comprising a hollow three-dimensional object containing a lumen in which 2 to 10 lymph node fragments are immobilized,
wherein the lymph node fragments include slices of a lymph node with a thickness not more than 2 mm, and/or pieces of a lymph node with a diameter not more than 3 mm.

17. The implant according to claim 16, wherein the lymph node fragments are immobilized by fibrin or hyaluronic acid.

18. The implant according to claim 16, wherein the lymph node fragments are immobilized by being embedded in a proteinaceous matrix.

19. The implant according to claim 16, wherein the lymph node fragments are immobilized by having been wedged into cavities present within the hollow three-dimensional object.

20. The implant according claim 16, wherein the lymph node fragments include slices of a lymph node with a thickness not more than 1 mm, and/or pieces of a lymph node with a diameter not more than 2 mm.

21. The implant according to claim 16, wherein the biodegradable scaffold has a tubular shape.

22. The implant according to claim 21, wherein the tubular shape has a surface with a longitudinal slit.

23. An implant for the formation and/or regeneration of a lymph node in the body of a patient in need thereof, said implant comprising:
- a biodegradable scaffold comprising a hollow three-dimensional object containing a lumen in which 2 to 10 lymph node fragments are immobilized, wherein the biodegradable scaffold comprises:
- a) polycaprolactone, polyglycolide, polylactide, or poly (1,3-trimethylene carbonate), or
- b) a copolymer of polycaprolactone and either polytrimethylene carbonate or polylactide, or
- c) a copolymer of polycaprolactone, polylactide and polyglycolide.

24. An implant for the formation and/or regeneration of a lymph node in the body of a patient in need thereof, said implant comprising:
- a biodegradable scaffold comprising a hollow three-dimensional object containing a lumen in which 2 to 10 lymph node fragments are immobilized,
- wherein the biodegradable scaffold comprises holes and/or pores through the three- dimensional object, the holes and/or pores having a diameter of 20 µm to 2 mm.

* * * * *

UNITED STATES PATENT AND TRADEMARK OFFICE
CERTIFICATE OF CORRECTION

PATENT NO. : 10,736,987 B2  
APPLICATION NO. : 15/538654  
DATED : August 11, 2020  
INVENTOR(S) : Kwak et al.

Page 1 of 1

It is certified that error appears in the above-identified patent and that said Letters Patent is hereby corrected as shown below:

In the Claims

In Column 16, Line 4:  
Replace "implanat"  
With --implant--

In Column 16, Line 23:  
Replace "The methold"  
With --A method--

In Column 16, Line 24:  
Replace "generation"  
With --regeneration--

In Column 16, Lines 26-27:  
Delete "immobilizing 2 to 10 lymph node fragments with the lumen;"

Signed and Sealed this  
Twentieth Day of October, 2020

Andrei Iancu  
*Director of the United States Patent and Trademark Office*